US008911084B2

(12) United States Patent
Fernandez Martinez et al.

(10) Patent No.: US 8,911,084 B2
(45) Date of Patent: Dec. 16, 2014

(54) OPHTHALMIC INSTRUMENT FOR THE MEASUREMENT OF OCULAR REFRACTION AND VISUAL SIMULATION, AND ASSOCIATED METHODS OF MEASUREMENT OF OCULAR REFRACTION, SIMULATION OF OPHTHALMIC ELEMENTS, VISUAL SIMULATION AND FOR OBTAINING OPTICAL PARAMETERS (75) Inventors: Enrique J. Fernandez Martinez, Murcia (ES); Pedro Prieto Corrales, Murcia (ES); Pablo Artal Soriano, Murcia (ES)

(73) Assignee: Universidad de Murcia, Murcia (ES)

( * ) Notice: Subject to any disclaimer, the term of this patent is extended or adjusted under 35 U.S.C. 154(b) by 228 days.

(21) Appl. No.: 13/392,723

(22) PCT Filed: Jul. 7, 2010

(86) PCT No.: PCT/ES2010/070467
§ 371 (c)(1),
(2), (4) Date: Feb. 27, 2012

(87) PCT Pub. No.: WO2011/023841
PCT Pub. Date: Mar. 3, 2011

(65) Prior Publication Data
US 2012/0154742 A1    Jun. 21, 2012

(30) Foreign Application Priority Data
Aug. 28, 2009    (ES) .................................. 200901809

(51) Int. Cl.
A61B 3/08    (2006.01)
A61B 3/14    (2006.01)
A61B 3/10    (2006.01)
A61B 3/00    (2006.01)
A61B 3/107    (2006.01)

(52) U.S. Cl.
CPC ............. *A61B 3/0025* (2013.01); *A61B 3/1015* (2013.01); *A61B 3/107* (2013.01)
USPC ........................... 351/201; 351/209; 351/211

(58) Field of Classification Search
USPC .................................................. 351/200–247
See application file for complete search history.

(56) References Cited

U.S. PATENT DOCUMENTS 7,281,796 B2 * 10/2007 Sumiya .......................... 351/205
7,448,752 B2 * 11/2008 Levine .......................... 351/205

(Continued)

OTHER PUBLICATIONS

Fernandez, E.J., et al., "Binocular Adaptive Optics Visual Simulator: Understanding the Impact of Aberrations on Actual Vision," Proceedings of the SPIE, vol. 7550, pp. 755014-1-755014-4, (2010).

(Continued)

*Primary Examiner* — Ricky Mack
*Assistant Examiner* — Robert E Tallman
(74) *Attorney, Agent, or Firm* — Oblon, Spivak, McClelland, Maier & Neustadt, L.L.P.

(57) ABSTRACT

An ophthalmic instrument for measurement of ocular refraction and visual simulation and a method of measurement obtaining the ocular refraction in a binocular manner, which incorporates a digitally controlled phase modulator for generating best ophthalmic correction in each subject. The instrument enables measuring refraction, not only associated with blurring and astigmatism, but also optical aberration of any order. The phoropter can simulate vision by any phase profile, including those of a diffractive or discontinuous type. The instrument also incorporates a subsystem for presentation of stimuli that produces stereoscopic vision of the same, enabling the subject to enjoy a three dimensional perception during the process, and two output pupils. The instrument, by its electro-optical features, enables simulation of vision as it would be modified after submitting an eye to different surgical techniques, such as refractive surgery or interocular lens implantation.

32 Claims, 8 Drawing Sheets

(56) References Cited

U.S. PATENT DOCUMENTS

2008/0284979 A1* 11/2008 Yee et al. .................... 351/209
2010/0262128 A1* 10/2010 Vogler .......................... 606/4

OTHER PUBLICATIONS

Fernandez, E.J., et al., "Binocular adaptive optics visual simulator," Optics Letters, vol. 34, No. 17, pp. 2628-2630, (Sep. 1, 2009).

Canovas, C., et al., "Hybrid adaptive-optics visual simulator," Optics Letters, vol. 35, No. 2, pp. 196-198, (Jan. 15, 2010).

Rocha, K.M., et al., "Enhanced Visual Acuity and Image Perception Following Correction of Highly Aberrated Eyes Using an Adaptive Optics Visual Simulator," Journal of Refractive Surgery, vol. 26, No. 1, pp. 52-56, (Jan. 2010).

Krueger, R.R., et al., "Novel applications of an adaptive optics visual simulator in the clinical setting," Proceedings of the SPIE, vol. 7550, pp. 755013-1-755013-15, (2010).

Rocha, K.M., et al., "Effects of Zernike Wavefront Aberrations on Visual Acuity Measured Using Electromagnetic Adaptive Optics Technology," Journal of Refractive Surgery, vol. 23, pp. 953-959 (Nov. 2007).

Manzanera, S., et al., "Liquid crystal Adaptive Optics Visual Simulator: Application to testing and design of opthalmic optical elements," Optics Express, vol. 15, NR. 24, pp. 16177-16188, (Nov. 26, 2007) (abstract only).

Artal, P., et al., "Adaptive-Optics System to Predict the Impact of Aberrations in the Quality of Vision," ARVO Annual Meeting Abstract Search and Program Planner, vol. 2002, Total 1 page, (2002) (abstract only).

Fernandez, E.J., et al., "Adaptive optics visual simulator," Journal of Refractive Surgery, vol. 18, No. 5, pp. 5634-5638, (Sep.-Oct. 2002) (abstract only).

International Search Report Issued Oct. 18, 2010 in PCT/ES10/70467 Filed Jul. 7, 2010.

\* cited by examiner

OPHTHALMIC INSTRUMENT FOR THE MEASUREMENT OF OCULAR REFRACTION AND VISUAL SIMULATION, AND ASSOCIATED METHODS OF MEASUREMENT OF OCULAR REFRACTION, SIMULATION OF OPHTHALMIC ELEMENTS, VISUAL SIMULATION AND FOR OBTAINING OPTICAL PARAMETERS

FIELD OF THE INVENTION

The present invention refers to an instrument for the measurement of advanced ocular refraction, preferentially in a binocular manner, and of visual simulation. Thus the apparatus pertains to the family of instruments known as phoropters. In these instruments a finite collection of lenses can be interchanged in a simultaneous manner to the vision on the part of the patient of visual stimuli or tests. In this way it can be discerned which optical corrections (limited to combinations of blurring and astigmatism) provide the best visual perception for each subject.

The present invention also refers to a method for the measurement the ocular refraction of the eyes, to a method of simulation of ophthalmic elements, to methods of obtaining optical parameters and to methods of simulation of vision.

The object the present invention does not employ moveable parts associated with the changing of lenses, but rather pertains to those systems in which the effect of the different corrections is produced by means of a spatial phase modulator or any other electro-optical element. Thus it is an electro-optical phoropter with a technology based on digital phase control. Therefore the invention also refers to a method that incorporates what may be identified as wavefront engineering.

The present invention likewise enables the simulation of vision by means of any optical element. Thus it is related to the so called visual simulators. In particular the instrument has the possibility of generating scenes that are perceived by the patient in a three dimensional manner during the measurement of the refraction or the simulation of ophthalmic elements, all of the foregoing in an electro-optical manner.

The invention is related to the subjective measurement of the visual quality of the subjects and the limits of their vision, all in a binocular manner. Thus it pertains to the field of biomedical instruments apt for the study, diagnostics and characterization of vision. To this end the instrument employs the concept of optical aberrations as a means of characterizing the effects of the different optical elements that can be simulated.

The invention refers to an instrument that enables the study, characterization and integral diagnostics of the vision in a digitally controlled manner from a subjective or perceptive viewpoint by means of visual stimuli.

The invention explicitly describes the practical embodiment of a phoropter type ophthalmic instrument that implements said methods and its equivalent practical implementations which produce the same effects and advantages.

BACKGROUND OF THE INVENTION

The measurement of refraction, or visual ametropia (blurring and/or astigmatism of the eye), is a requisite step before correcting the same. The quality of vision is of utmost importance for the well-being of a person, because it is estimated that human beings receive about 80% of the information of their surrounding by the sense of vision.

A large percentage of the population suffers some ametropia, and in some cases there exists a notable variation in incidences depending on the geographic region. For example, it is a known fact that among Asiatic populations there is up to an 85% incident rate for myopia in certain regions of the continent. It also occurs that the eye undergoes a series of changes due to age related developments, which result in a loss of the ability to correctly focus on objects located at different distances. What is known as presbyopia or tired eyes affects 100% of subjects over 50 years old.

In light of the above the conclusion may be drawn that the measurement of visual defects caused by refractive ametropia is a field meriting worldwide interest with a potential market that embraces 100% of the population.

An issue that is inseparably linked to the measurement of ocular refraction is the available visual corrections. The characteristics of these determine the requisite quality and precision for measuring visual quality.

A quick historical review of visual corrections starts with the first ophthalmic lenses that corrected blurring, and which began to be used more extensively beginning in the thirteenth century, especially for compensating presbyopia or tired eyes that appears in the human eye at about the age of 50 and onward. Astigmatism was not adequately measured and corrected with cylindrical lenses until the nineteenth century, all indications being that the pioneer in the method was the renowned scientist Thomas Young. Since then the advances made to ophthalmic lenses have been modest. Nowadays, the large majority of subjects who use eyeglasses or contact lenses, which made their appearance around the mid twentieth century, only correct their blurring and/or astigmatism.

It was not until well into the twentieth century that the first methods of subjective measurement of the optical quality of the human eye appeared, clearing revealing the existence of other optical defects or aberrations that compromise the quality of vision, besides the already known blurring and astigmatism.

Among the numerous existing methods and techniques, the Hartmann-Shack sensor may be mentioned due to the large acceptance and widespread use it currently has. The first reference to its use on the human eye appears in the works of Liang, B. Grimm, S. Goelz, and J. F. Bille, "Objective measurement of WA's of the human eye with the use of a Hartmann-Shack wave-front sensor," J. Opt. Am. A 11, 1949-1957 (1994); J. Liang and D. R. Williams, "Aberrations and retinal image quality of the normal human eye," J. Opt. Soc. Am. A 14, 2873-2883 (1997); and also P. M. Prieto, F. Vargas-Martin, S. Goelz, P. Artal, "Analysis of the performance of the Hartmann-Shack sensor in the human eye", J. Opt. Soc. Am. A, 17, 1388-1398 (2000). Nowadays there are commercial versions that implement this method with much success in certain applications.

The possibility of objectively measuring the aberrations favoured the appearance of adaptive optics applied to the human eye at the start of the twenty first century. By means of this technique the optical aberrations can be corrected in a precise manner and in real time following their measurements. This is obtained by means of the use of phase modulators which can be based on the use of liquid crystal or deformable mirrors, in all of their variants and modalities. A pioneering work in this field was published by E. J. Fernández, I. Iglesias, and P. Artal, "Closed-loop adaptive optics in the human eye", Opt. Lett, 26, 746-748 (2001). This technique is the most immediate predecessor to the so called visual simulators. These are instruments that enable the measurement of the optical quality of the eye, and its manipulation by means of aberration generating devices. To date it use has been restricted to the field of scientific research and, preferably, to monocular cases. An early work in this field was described in E. J. Fernández, S. Manzanera, P. Piers, P. Artal, "Adaptive optics visual simulator", J. Refrac. Surgery, 18, 634-638 (2002).

The measurement of higher level optical aberrations, beyond blurring and astigmatism, has opened the door to its possible correction by means of ophthalmic elements, such as lenses, contact lenses, intra-ocular lenses that are surgically implanted in the eye of the patient, or refractive cornea surgery, in which different profiles can be sculptured on the cornea of the subject for its refractive correction.

However, it is now known that the refraction does not provide an objective measurement of the optical quality of the eye in an absolute sense. Although optical quality is strongly linked to the quality of vision, there are no methods that are capable of estimating the sharpness or sensibility to contrast of a subject based on the values of the different optical parameters that characterize the eyes. Recent works have clearly demonstrated this limitation, as shown in the article of P. Artal, L. Chen, E. J. Fernández, B. Singer, S. Manzanera, D. R. Williams, "Neural compensation for the eye's optical aberrations", J. Vis., 4, 281-287 (2004). This is easy to understand when the phenomenon of vision is undertaken in an integral manner. Thus, the formation of images in the retina only constitutes the first step of a very complex process which involves the transduction of light into physical-chemical signals that are sent to the brain, and a subsequent psychological interpretation of them which ultimately produces the visual sensation or perception. In this manner, it is accepted that the measurement of refraction has a strong subjective component that bears on the treatment of the patient, who ultimately must decide which correction gives him the best visual perception.

In this context we find that, despite the enormous advances of the last few years in the measurement of optical quality of the eye, traditional phoropters, those based mainly on conducting simple visual tests by means of lenses with different graduations until the subject perceives the best image, continue to be the most used throughout the world.

These phoropters could be grouped together as a first classification of those which are placed in front of the eyes of the subject, like some eyeglasses. These incorporate a series of purely mechanical controls that enable rotating astigmatic lenses to position them correctly, as well as the interchange of spherical lenses for the correction of simple blurring, and which are currently the most utilized type of phoropters in clinical practice throughout the world. Other alternatives, essentially variants of the same concept, enable the introduction of colour filters, polarizing filters, etc. In all of them the visual tests or stimuli are projected before the subject on a screen or similar, in an independent manner with respect to the phoropter per se.

Within this family of instruments for the measurement of ocular refraction we find numerous patent documents, such as document US 2 003 009 063 A1, which introduces improvements for the correct control of the variables that could be adjusted in the phoropter by the examiner in very low lighting conditions.

Document U.S. Pat. No. 7,156,517 B2 shows various improvements which above all affect the ergonomics of the examiner, allowing him to be more comfortable during the control of the lenses that he is introducing into the phoropter in order to measure the ocular refraction. This is obtained by means of new lighting systems. In any event, this is an invention that does not disclose direct improvements for the patient or subject who is undergoing the refraction tests.

Document U.S. Pat. No. 5,812,241 A discloses a much more compact phoropter in which the spherical and astigmatic lenses are directly incorporated into a type of interchangeable roulette, organized in such a way that it reduces the size of the instrument. Again, as in the previous document, this is an invention that provides a modest benefit to subject who is undergoing the refraction tests. In any event, the proposed instrument follows along the same lines as this family of phoropters.

The same idea for improving the interchange of ophthalmic lenses by means of a reel that holds them, and in particular, disclosing a method that makes its control more efficient, is described in document JP 8 182 649 A, for a phoropter with two rotational channels by means of a mount adapted specifically for this use.

The invention disclosed in document U.S. Pat. No. 4,861,156 introduces a control unit for visual stimuli that are shown to the subject during the use of the phoropter. Basically this enables controlling the visual tests with the phoropter itself, avoiding the need of the examiner to change positions during the process, thus improving his comfort.

The phoropter described in document U.S. Pat. No. 5,223,864 introduces some sensors in the lenses themselves, which make it possible to find, for example, the angle that an astigmatic lens is using, within the scheme of the classic phoropter described in all of the previous documents of this type. Consequently, this is an invention that improves the manipulation of the instrument on the part of the examiner.

More recently the first phoropters controlled electronically by means of special lenses have made their appearance, the strength of which depends on the electrical signal sent. The concept here is different from that of the family of phoropters presented above, in which the trial lenses are mechanically interchanges during the refraction process. This is done by substituting the lenses either by rotation or by switching them. With electro-activated phoropters that make possible the practical implementations described in documents U.S. Pat. Nos. 7,264,354 B2 and 7,533,993 B2, the examiner can adjust the correction applied to each patient during the process in a digital manner, which, consequently, is much more precise than previous methods. Furthermore, the smallest step or resolution which refraction can obtain now depends on the minimal electrical signal that can be sent to control the strength of the lens. In these instruments the measurement of astigmatism is not obtained by means of variable strength lenses, and so for this ametropia it is still necessary to recur to the previous methods of mechanically interchanging and rotating the lenses.

Document U.S. Pat. No. 4,943,162 discloses an invention that facilitates the use of lenses with astigmatism in the context of a phoropter. The invention proposes a method and instrument that implements it for the rotation of two series of astigmatic lenses in a systematic manner to determine the refraction of the subject.

In current state of the art there is clearly an enormous breach between modern means of correction of ametropic refractions, and of optical aberrations in general, with the measurement of the refraction or the subjective quality of vision. Thus, nowadays adequate technology exists for manufacturing ophthalmic lenses and contact lenses with phase profiles that go beyond blurring and astigmatism. Intraocular lenses with aspheric profiles are already being mass produced, including the diffractive type for surgical implantation. Along the same lines, modern surgical techniques in refractive surgery, by means of the latest generation of lasers with sophisticated guidance systems, enable trimming the cornea of the patients with high precision, thus opening the door to high order correction of optical aberrations.

However, as has previously been made manifest, the capacity and operation of current phoropters is quite removed from providing the necessary features for evaluating the vision of the patents, on the one side in a entirely digital manner, and on the other by incorporating the possibility of seeing through the phase profiles, or correction, beyond blurring and astigmatism, which can limit in a substantial manner the development of new corrections systems.

SUMMARY OF THE INVENTION

The object of the invention, therefore, is to provide an ophthalmic instrument for the measurement of ocular refraction and visual simulation that overcomes the shortcomings and limitations of the prior art.

The invention provides an ophthalmic instrument for the measurement of ocular refraction and visual simulation that enables the simultaneous presentation of visual stimuli and their perception through different phase profiles or aberrations which comprise:

a system of presentation of stimuli which in turn comprises two input pupils, two output pupils, and at least one phase modulator, which is optically conjugated with the two input pupils and the two output pupils of the instrument, in which the phase modulator is capable of producing any phase profile and functions of the measurement of refraction and simulation of ophthalmic elements or visual conditions done in a binocular manner.

The present invention discloses a method for the measurement of ocular refraction in a binocular manner, based on the use of an instrument that incorporates a phase modulator that produces the best optical correction for the compensation of ametropia, and of a subsystem for presentation of visual stimuli. The instrument enables the object method of the invention to work as an electro-optic phoropter in which the search for the best correction is done in a computerized manner.

Furthermore the invention discloses a method for the simulation of vision by means of any optical element that may be used in conjunction with the eyes. This last feature enables the instrument to provide the best personalized correction for each subject who looks through it. At the same time it favours the design of new ophthalmic elements adapted to the optics of each eye in particular, and in each vision situation: nocturnal, close up, etc.

The present invention discloses a method for the evaluation of the quality of the vision and the search for the best refraction, by means of a phoropter type instrument that operates without moving parts, and that is capable of producing any phase profile, thus resolving the technical limitations that affect the latest generations of this invention, all the foregoing controlled in a digital manner. Thus, the instrument enables the simulation of any ophthalmic element without any limits for the phase that is introduced. Furthermore the visual tests or stimuli can be presented in a stereoscopic form producing a three dimensional perception of the scene employed for the search and measurement of the ocular refraction.

The instrument that implements the present invention fosters a practical, compact implementation with a relatively small number of elements. The use of lenses aligned along different optical axes enables the formation of two telescopic system that optically conjugate three separate planes by means of the utilization of only three lenses or, with the same result, spherical mirrors.

The instrument enables the modification of the aberrations through which the subject perceives a series of visual stimuli by means of a single aberration generator or phase modulator. This is controlled digitally from a computer. In this way the different corrections for the compensation of myopia, hyperopia, astigmatism and presbyopia or tired eyes are generated without the need to incorporate new elements into the system, and without the manipulation of moving parts. The phase modulator not only enables obtaining corrections for the different ametropias based on the modification of the blurring or astigmatism, but also any aberration phase profile of the highest order can be incorporated and the vision stimulated through it.

The instrument can incorporate a device based on the use of liquid crystal, either ferroelectric or nematic, with their different versions of implementation such as liquid crystal on silicon, as a phase modulator element.

It is also possible to configure the instrument with a deformable mirror, in any of its variants and different technologies, such as electrostatic, bimorph, magnetic and independently moveable segmented mirrors comprised of several micro-mirrors.

With the same effect although more complex and expensive, the system can incorporate two phase modulator elements instead of one.

Once the subject has been placed in front of the instrument and the distance of the output pupils adjusted to the interpupillary distance, the lines of vision of each one of the eyes are adjusted without the need of moving parts in the system. This is done by means of the phase modulator which imprints the adequate inclination for the correct viewing of the stimulus to light beams aimed at each one of the pupils. To correctly centre the pupils of the subject in the instrument, an auxiliary positioning subsystem may be employed which is basically made up of a camera that forms images of the two pupils of the subject in a simultaneous manner.

The instrument which implements the present invention incorporates a screen controlled by a computer on which the visual stimuli are displayed. An obvious advantage of the instrument is the possibility of showing stimuli in a binocular manner. These can be classic stimuli found in optometric practice, such as patterns with different frequencies, letters or normalized characters, as well as real scenes such as landscapes, faces, etc.

In one embodiment of the instrument the visual stimuli may be displayed in a stereoscopic manner. In this modality the subject perceives the scene displayed by the screen or screens in a three dimensional form, which provides the visual test with total realism, as it is impossible for the eye to perceive the difference between a real three dimensional scene and one generated in the phoropter. In the detailed description of the invention different equivalent practical implementations are developed for generating stereoscopic images in the instrument.

In an alternative embodiment of the instrument, one of the telescopic systems is removed, leaving only the plane of the input pupils and that of the output pupils as conjugated planes in the phoropter. In this way a much more compact instrument is obtained without the loss of features, for which it is necessary to use a phase modulator that operates in transmission, or equally, a beam splitter placed immediately in front of the phase modulator in reflection to correctly guide the light issuing from the subsystem for presentation of visual stimuli towards the subject.

The instrument object of the present invention can function in monocular mode, just as classic phoropters operate, simply by occluding one of the eyes. For this there is no need to use additional elements in the system or moving parts, but rather the phase modulator device can generate this effect. In an alternative embodiment of the instrument, the function of occlusion is obtained by means of a matrix of micro-mirrors placed in front of the subsystem for presentation of visual stimuli.

The invention also discloses a method for visual simulation of any optical element. The instrument likewise enables the simulation of vision following a hypothetical surgery that affects or alters the refractive state of the eye, such as occurs in cataract surgery, intraocular lens implantation, or refractive surgery in general. Thus it provides an important application as a pre-surgical visual trial and testing step prior to eye surgery.

Other features and advantages of the present invention will be disclosed in the detailed description that follows of an illustrative embodiment of its object in relation to the accompanying Figures.

The following numbered references are linked to the different physical elements which integrate the invention, as will be seen throughout the present document:

1. System for presentation of visual stimuli.
2. Screen for presentation of stimuli.
3. Beam of light aimed at the right eye, together with 4
4. Beam of light aimed at the left eye, together with 3
5. Collimator objective of the screen for the visual stimuli
6. Input pupils
7. Lens
8. Flat mirror
9. Phase modulator in reflection
10. 9 bis Phase modulator in transmission
11. Lens
12. Lens
13. Internal reflection prism for the right eye, together with 13
14. Internal reflection prism for the left eye, together with 12
15. Output pupil for the left eye, together with 15
16. Output pupil for the right eye, together with 14
17. Optical axis of lens 11
18. Optical axis of lens 10
19. Beam splitter for the control of the position of the pupils
20. Lens collimator for the control of the position of the pupils
21. System for the control of the position of the pupils
22. Camera for the control of the position of the pupils
23. Beam splitter
24. Frontal view of the system of micro-mirrors
25. System of micro-mirrors
26. Simple image on the screen
27. Panel separator
28. Light source
29. Objective for the stimuli aimed at the right eye, together with 29
30. Objective for the stimuli aimed at the left eye, together with 28
31. Simple image on the screen for the right eye, together with 31
32. Simple image on the screen for the left eye, together with 30

DETAILED DESCRIPTION OF ONE FORM OF THE PREFERRED EMBODIMENT OF THE INVENTION

The invention disclosed consists in a method that enables obtaining the refraction of the subject in a binocular manner and the electro-optic instrument that implements it in the form of a phoropter. The method likewise enables the simulation of the most adequate correction for a previously detected ametropia, as well as any other ophthalmic element or visual condition in general.

Figure 1:
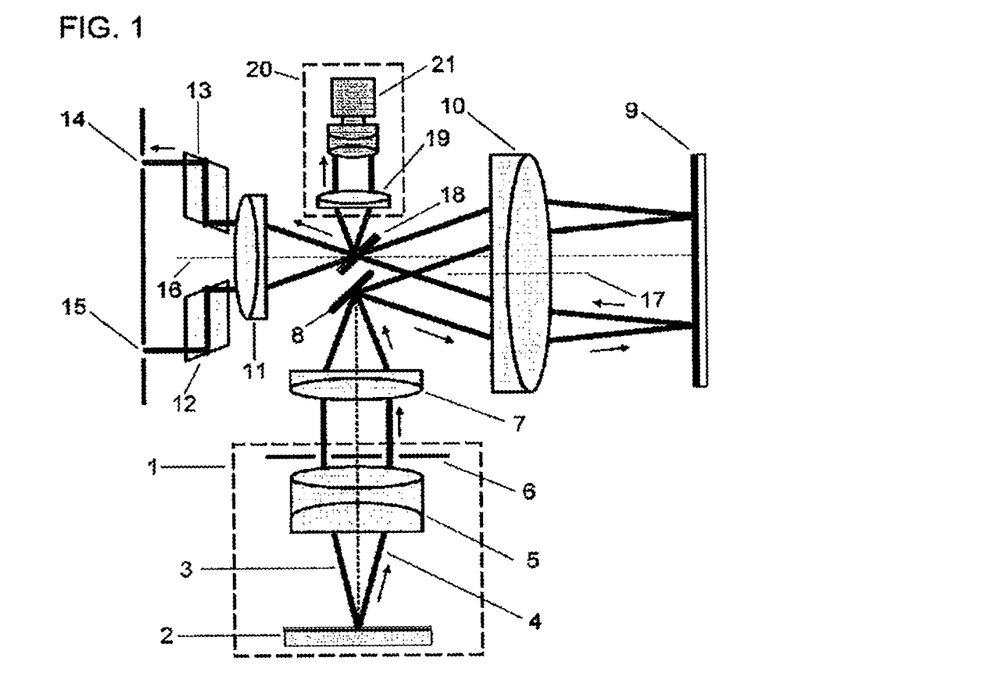
FIG. 1 shows a schematic view of the basic parts of the ophthalmic instrument of the invention for putting into practice the method of measurement of refraction in a binocular manner and the simulation of ophthalmic elements in accordance with the present invention, which includes a device for the generation of phase profiles and a monitor for the display of visual stimuli. The schematic also includes an additional path for monitoring the pupils of the subject.

The basic parts for the practical implementation of the instrument or phoropter that enables the object method of this invention is shown in a schematic way in FIG. 1. The system of FIG. 1 incorporates a subsystem for presentation of visual stimuli (1). Said subsystem (1) consists, in the first place, of a screen or micro-screen (2) where the scenes or images (25) to be presented to the subject are shown (an example of image (25) can be seen in FIG. 6). Screen (2) is controlled by a computer, from where images (25) are generated and programmed. Subsystem for presentation of visual stimuli (1) likewise incorporates an objective (5) that collimates the light issuing from screen (2), forming an image at infinity. Objective (5) can be a dioptic system formed by several surfaces and lenses, or, in its simplest version, by a single lens. The use of a more sophisticated objective that incorporates diverse surfaces enables the correction of aberrations in a more efficient manner, with the drawback of increasing the complexity of element (5). Effective input pupils (6) of the system, which limit the amount of light issuing from a point located on screen (2) and on the optical axis of the collimating lens or objective (5), are placed immediately after said element (6) in a direction of the light issuing from stimuli screen (2). The direction of the light is shown by means of arrows in FIG. 1.

Input pupils (6) of the instrument distribute the light that the optical system directs towards one or the other eye of the subject that is being measured by means of the method and phoropter disclosed in the invention. For this a mask can be used in which two symmetric orifices are made with respect to the optical eye of objective (5) and having the same size. In FIG. 1 the path of the light that reaches left eye (4) has been indicated with arrows along a main beam, and the beam without arrows corresponds to right eye (3). The input pupils of the eyes of the subject are positioned on output pupils (14, 15) of the instrument. This pupils are the images of the two input pupils (6) along the entire optics that follows them in the apparatus. Therefore there are two output pupils (14, 15) one for the left eye and the other for the right eye, respectively. The light of subsystem for presentation of visual stimuli (1) is redirected to the rest of the instrument by means of positive lens (7). The distance between said lens (7) and input pupils (6) of the phoropter is exactly the focal distance of the lens. In the practical implementation of the instrument, lens (7) may be substituted with the same effect by a spherical or parabolic mirror having a similar focal distance, and which can be aligned on or outside of its rotating axle. By means of flat mirror (8) the beams corresponding to each of pupils (14, 15) are sent to the following lens (10). The purpose of mirror (8) is to make the instrument more compact, although its implementation is not fundamental for the functioning of the instrument.

The first two lens (7, 10) of the phoropter are deployed in an afocal manner, that is, forming a telescope. For this, the focal image of first lens (7) is located exactly on the focal object of second lens (10). This way enables optically conjugating the focal object plane of first lens (7) on the focal plane image of second lens (10). It is precisely on this focal plane image of second lens (10) where phase modulator device (9) is positioned. Phase modulator or generator (9), or aberration generator, is a device that employs, preferably, liquid crystal for the manipulation of the wavefront phase. The positioning of two first lenses (7, 10) enables input pupils (6) of the system to remain conjugated, or projected on the surface of phase modulator (9); exactly on the corresponding surface of each one of the images of input pupils (6) on phase modulator (9), on which are generated and, in general, manipulated in a controlled manner from a computer the phases that affect the stimuli images emerging from screen (2) that the subject who is looking through the phoropter finally perceives. Without losing any features and maintaining the same effect, phase modulator (9) based on the use of liquid crystal can be replaced by a deformable mirror, the operation of which is based on the mechanical modification of the mirrored surface, in a controlled manner, in order to manipulate the phase of the incident radiation. In the same way, the system can be implemented, obtaining the same results, with two devices or phase modulators (9) dedicated in a simultaneous manner, to each one of the images of input pupils (6) of the instrument, positioned in the same focal image plane of second lens (10). This can be replaced in the apparatus by a spherical or parabolic mirror with a similar focal distance, resulting in the same effect on the system.

After the reflection of the light in phase modulator (9) directed at each one of the output pupils of the instrument, the beams again find second lens (10) in their path and the last and third lens (11) of the phoropter. This pair of lenses (10, 11) is found in an afocal configuration, forming a telescopic system, in a way similar to what was described for the pair formed by first lens (7) and second lens (10) of the system. The focal image of second lens (10) corresponds with the focal object of third lens (11). This enables the forming of an image of, or optically conjugate, the projection of input pupils (6) on phase modulator (9) on the plane of output pupils (14, 15) of the instrument. The net effect along the entire phoropter is that of optically conjugating pupils (6) positioned on subsystem for presentation of stimuli (1), on output pupils (14, 15), or, what is the same, on the pupils of the subject who watches through the instrument. Third lens (11) can be substituted, obtaining the same effect, by a spherical or parabolic mirror having the same focal distance. For the purpose of employing said second lens (10) of the system on the telescopes formed by first lens (7) and third lens (11) with second lens (10), it is aligned outside optic axle (16) that third lens (11) defines. Thus, optical axis (17) of second lens (10) ends up displaced, as is FIG. 1 shows. The system can also operate, with the same effect, with two lenses in front of phase modulator (9), one for the light emitted from subsystem for presentation of visual stimuli (1), and the other for the light reflected by phase modulator (9). This configuration increases the number of optical elements needed, and increases the size and weight of the whole system.

The beams that cross third lens (11), corresponding to each of input pupils (6) of the system, emerge at a fixed distance, which depends on the relation of increases defined for the purpose between the focal points of the different lenses that comprise the system, once the separation of input pupils (6) of the phoropter is established. Thus, to couple this distance to the interpupillary separation of a subject who watches by means of the phoropter, the incorporation of additional elements becomes necessary. For this, some prisms (12, 13) can be employed, which operate in full reflection, as is shown in FIG. 1. The separation between these prisms (12, 13) should be adjustable so that the operator of the instrument may adjust the final separation of the beam to the interpupillary distance of each subject who looks through the phoropter. Prism (12, 13) can be replaced by pairs of flat mirrors, with the same effect or combinations of prisms and mirrors.

To correctly centre the pupils of the subject on output pupils (14,15) of the phoropter, an auxiliary positioning subsystem (20) may be employed. Said auxiliary positioning subsystem (20) is basically comprised of a lens (19), and an objective coupled to a camera (21). In this way camera (21) simultaneously registers the two pupils of the eyes of the subject. It positioning may be carried out in an automatic and systematic manner, until they are moved to the positions of reference defined by the placement of output pupils (14, 15) of the instrument. To collect the light from the pupils of the subject, a beam splitter (18) is used, located in the proximity of or on the focal object of third lens (11) of the phoropter. There is also the possibility of replacing auxiliary positioning subsystem (20) with a wavefront sensor, which enables the objective measurement of the optical quality of the eyes of the subject in a binocular manner.

Figure 2:
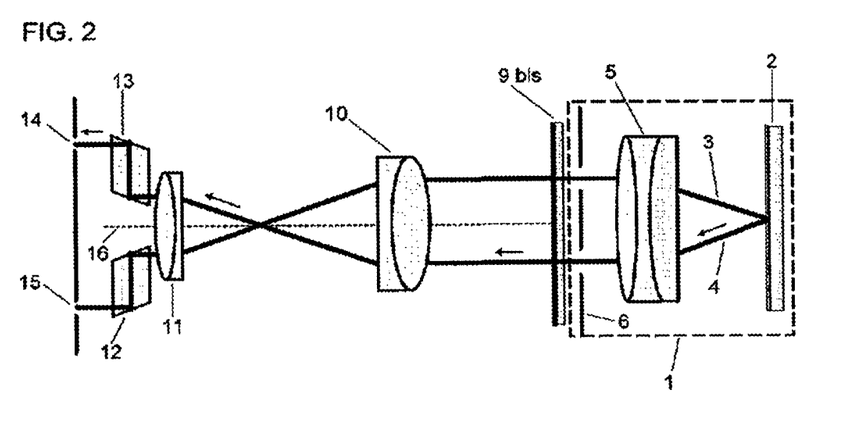
FIG. 2 shows a schematic view of the main components for putting into practice the method of refraction in a binocular form and the simulation of ophthalmic elements in accordance with the present invention in its simplified mode of operation with a phase generator device that enables its operation in transmission.

Just as is shown in a schematic way in FIG. 2, phase modulator (9) of liquid crystal may also be operated as a phase modulator in transmission (9 bis). In this case the experimental system can be notably simplified, operating with the same effect without the need of adjusting the first two lenses (5, 10) or the conjugation of input pupils (6) of the system on the surface of phase modulator in transmission (9 bis). In this simplified case input pupils (6) are placed directly in front of phase modulator in transmission (9 bis) in the direction of the light emitted by screen for presentation of stimuli (2). The rest of subsystem (1) for the presentation of visual stimuli is left just as has been previously described in FIG. 1. An important advantage of this modality of the instrument, operating with phase modulator in transmission (9), is the greater simplicity of the experimental assembly and the possibility of putting together more efficient optical elements that promote a smaller size and weight of the phoropter.

Figure 3:
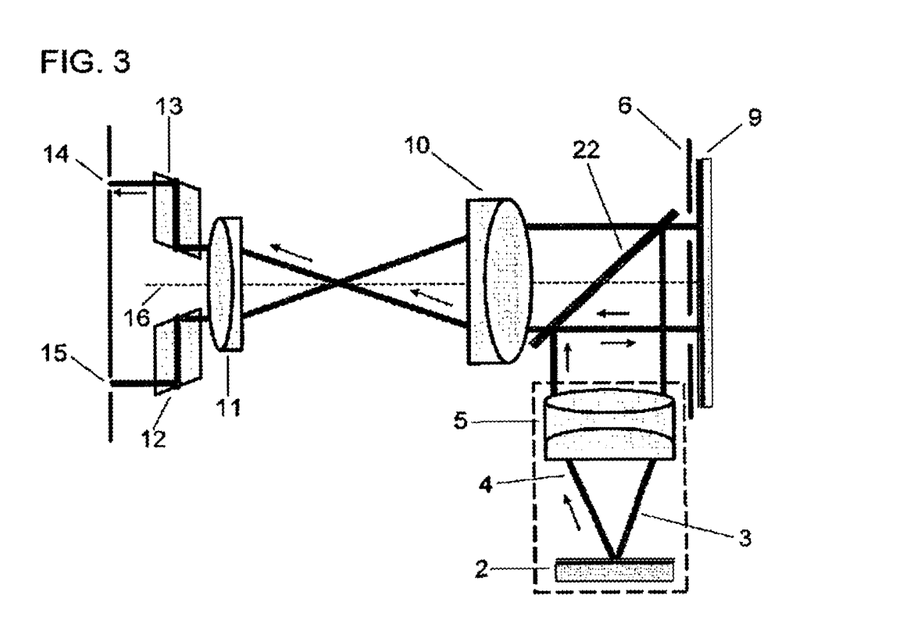
FIG. 3 shows a schematic view of the main components for putting into practice the method of refraction in a binocular form and the simulation of ophthalmic elements in accordance with the present invention in its simplified mode of operation with a phase generator device that functions in reflection and that has a light splitter placed in front of the same for guiding the light issuing from the path of the presentation of stimuli.

FIG. 3 includes another possibility of the practical implementation of the instrument which enables omitting first lens (7) to obtain a compact version of the invention. In this version beam splitter (22) is placed between lens (10) and phase modulator (9) in order to redirect part of the light issuing from screen for presenting stimuli (2) to the surface of phase modulator (9). Immediately in front of the surface of phase modulator (9) input pupils of the system (6) are placed. Beam splitter (22) may be replaced by two others with a smaller size which, at all events, cover each one of the beams aimed at each one of the pupils of the subject.

In order for the subject that is looking through phoropter to obtain a binocular perception of the stimulus displayed on screen (2) it is not enough for his two pupils to be located on output pupils (14, 15) of the instrument; rather it is necessary that the lines of vision or sight of said eyes excite the corresponding points on the retinas of the eyes. This requisite condition for binocular perception is obtained by imprinting to the beams that enter the eyes coming from a single object at an adequate inclination, imitating the real situation that occurs with natural scenes and the vision of a naked eye. This inclination can vary from subject to subject due to different causes, such as strabismus or phoria, etc. Through the use of adequate phase profiles phase modulator (9) makes it possible to provide the correct inclination for each subject.

Figure 4:
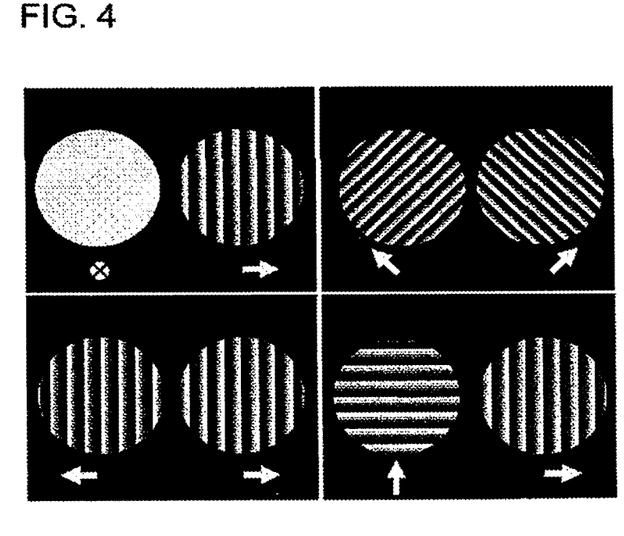
FIG. 4 shows, in the form of practical examples for illustrating the method disclosed in the present invention, different programmed phase profiles so that the patient may obtain the merger of the images through the phoropter disclosed in the invention, creating a binocular perception of the visual stimuli during operation of the same.

FIG. 4 shows by way of example some phases together with the displacing effect that they entail. Thus, the top mask on the left shows a pupil with constant phase which does not produce any effect in the vision in the right eye, together with a light inclination of the beam toward the temporal side of the eye on the left. This profile could possibly correspond to a person with exophoria in the left eye. The panel on the bottom left shows some phase profiles in the pupils that provoke a similar and temporal inclination of the beams in both eyes. This profile could correspond to a person with binocular exophoria. The panel on the top right shows a similar temporal and ascending displacement in both eyes as an example of a combination of several directions. The method enables the displacement of the beam in any direction in space without restrictions of the angle amplitude, and independently for each eye. The panel on the bottom right shows an ascending angle for the right eye and a lateral angle in the temporal sense for the left eye. This technique guarantees that all of the subjects who look through the phoropter obtain a genuinely binocular perception.

Figure 5:
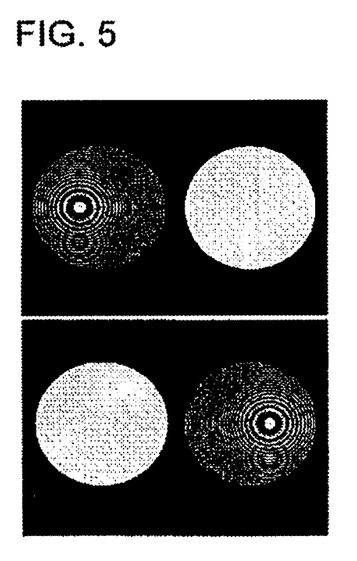
FIG. 5 shows, in the form of an example for illustrating the method disclosed in the present invention, two combinations of phase profiles created by means of the overlay of blurring and lateral displacement, which generates the net effect of occlusion of one of the eyes of the patient during the viewing of the stimuli.

Another feature of the system that brings numerous advantages and big potential is the possibility of carrying out purely optical ocular occlusions, as opposed to previous mechanical methods that consist in physically covering one of the eyes. This can be done by programming different phase profiles in modulator (9). FIG. 5 shows as an example some phase profiles that are a result of a combination of an angular displacement of the beam towards the temporal side and a blurring of 5 dioptres. The top panel shows a profile for the occlusion of the right eye and the bottom one corresponds to the left eye. The net effect of this profile is to provide a retinal image of the very blurry and very eccentric scene shown by screen (2) with respect to the fovea or central zone of vision. In this way the lack of perception of this image is guaranteed. The process of occlusion can be done with a frequency that is only limited by the refresh speed of phase modulator device (9).

Figure 6:
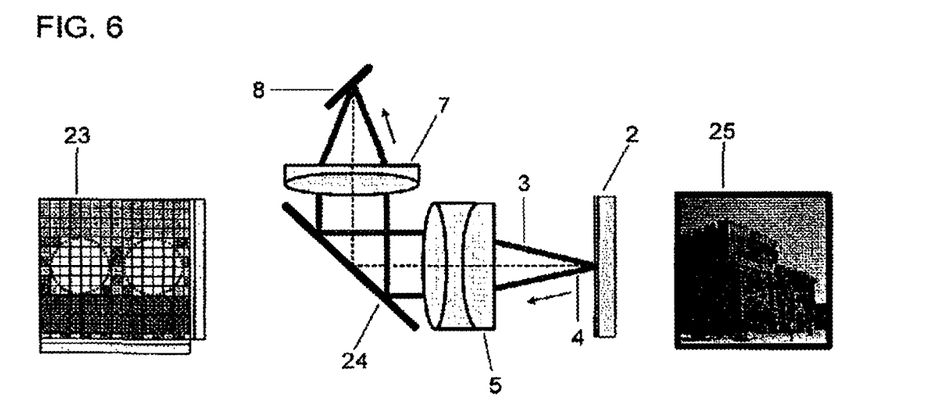
FIG. 6 shows a schematic view of the main components of the path of presentation of stimuli for putting into practice the method of measurement of the refraction in a binocular manner and simulation of the ophthalmic elements in accordance with the present invention in its mode of operation with a reflector device comprised of micro-mirrors that can be actuated in a controlled and independent manner so as to enable the generation, occlusion and control of the size and position of the effective output pupils from the phoropter system during operation of the same.

The phoropter can be implemented without input pupils (6) described above. A matrix of micro-mirrors can be incorporated in its place, a front view of which is depicted as (23), formed by a large number of mirrored facets, typically more than 100, the movement of which can be digitally controlled in an independent manner by means of a computer. Use of this device is visually depicted in FIG. 6. The light emerging from objective (5), which is in the subsystem for the presentation of visual stimuli, enters the rest of the phoropter by means of micro-mirror system (23) positioned in front of the first lens (7) of the instrument. Matrix of micro-mirrors (23) can produce a similar effect as generated by input pupils (6) based on the orifices in a opaque plate. For this the inclination of the micro-mirrors inscribed in each one of the chosen positions as input pupils, as seen in FIG. 6, left panel, reference (23), should be similar and enable the incident light to effectively enter the system. Conversely, the rest of the micro-mirrors should have inclinations such that they avoid the entry of the incident light on them. With this a net effect is obtained from the input pupils that has certain advantages with respect to the fixed implementation of a mask with two orifices. The underlying principle is the possibility of changing the size and position of the input pupils during the operation of the instrument. This enables carrying out a tracking of the pupils of the subject that ensures, for example, the entry of the light coming from the stimulus in whatever position it may be. On the other hand, it likewise provides an alternative method for the occlusion of one of the eyes by means of actuating on the angle of the micro-mirrors. The operation speed of the devices is in the range of kilo-hertz.

The phoropter also has the possibility of showing visual stimuli in three dimensions. To this end, different alternative embodiments of the instrument may be employed, which are detailed as follows. For the generation of stereopsis, or the sensation of depth and volume in the images, it is necessary to introduce images in the eyes with a certain degree of disparity, exactly as they are received in a natural setting. This basically occurs due to the difference in positioning of the eyes that exists with respect of the object and that produces slightly different retinal images, which in turn produce the perception of three dimensionality. The effect can be simulated in the object phoropter of the present invention by means of alternating occlusion of the eyes, synchronized with the apparition of disparate images (25) on screen for the presentation of stimuli (2). When the occlusions are done at frequencies above 30 Hz the visual system is not capable of perceiving them. The image appears continuous to the vision. This well known fact can be taken advantage of for generating the sensation of three dimensionality. The alternating occlusions can be done, always accompanied by the presentation of disparate images (25) for the purpose of binocularity, by means of the matrix of micro-mirrors (25), phase modulator (9), or in combination with both elements.

Figure 7:
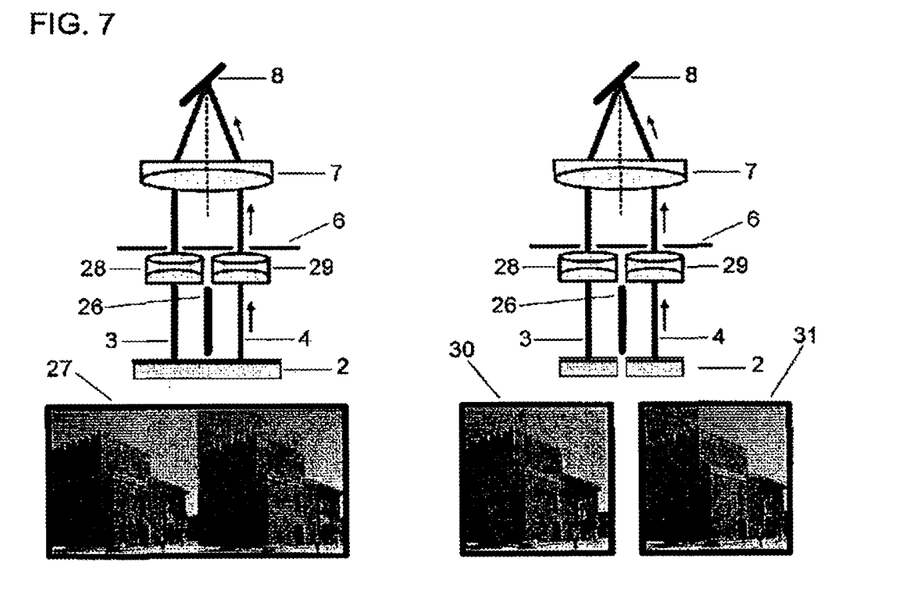
FIG. 7a shows a schematic view of the main components of the path of presentation of three dimensional stimuli for putting into practice the method of measurement of refraction in a binocular manner and simulation of the ophthalmic elements in accordance with the present invention in its mode of operation with a single screen and double image.
FIG. 7b shows a schematic view of the main components of the path of presentation of three dimensional stimuli for putting into practice the method of measurement of refraction in a binocular manner and simulation of the ophthalmic elements in accordance with the present invention in its mode of operation with two screens functioning simultaneously.

The sensation of depth or stereopsis can be obtained in the object phoropter of the present invention from other alternative modalities to the one disclosed above, and which are visually depicted in FIGS. 7a and 7b. One possibility consists in the use of two objectives (28, 29) in front of screen for presentation of stimuli (2). Each one of these is dedicated to the light that is sent to each one of the two pupils of the subject. The placement of opaque screen (26) avoids that the light of screen (2), which generates the stimulus for right eye (3), enters the objective dedicated to the left eye, and vice versa. In this implementation, screen (2) shows the stimulus with disparity in two clearly differentiated fields (27), as is shown in FIG. 7a. Another practical implementation of the invention makes use of two screens (30, 31) for the presentation of stimuli with disparity; this alternative is shown visually in FIG. 7b. The advantage of this alternative is based on the higher resolution which the stimuli can be presented, although it comes at a higher cost and complexity because it doubles the number of screens (30, 31).

The use of the instrument for obtaining refraction and simulation of ophthalmic elements and, in general, of any optical condition or situation can be carried out by means of the following procedure: The subject is initially positioned in a way that the pupils of his eyes coincide with output pupils (14, 15) of the phoropter. For this the operator, who possibly could also be the subject who looks through the phoropter, can manually or mechanically adjust the distance between prisms (12, 13) operating in reflection. To do so there is the option of employing auxiliary subsystem (20) for positioning the pupils. Once the position of the eyes of the subject on the phoropter is set, the visual stimulus is presented on screen (2) and the binocular vision of the same is attained. In the event there is some type of phoria or situation that impedes the correct binocular merger of images, in which case the subject perceives a double image of the stimulus, the operator proceeds to incline the beam of each one of the eyes, in the manner detailed in the description of FIG. 4. The protocol is executed until binocular perception is reached by progressively adjusting the inclination of each of the beams aimed at each eye. The fact that the control of the convergence or inclination of the beams is controlled in a digital manner by means of phase modulator (9) allows the subject to be able to actuate on his own by means of a computer program or application adapted to the situation. Otherwise and external operator can direct and control the process.

The ocular refraction can be obtained at any distance without doing more than programming the pupils projecting the corresponding blurring on phase modulator (9). As a practical example, refraction for long distance does not require any starting phase, whereas for a distance of 33 cm, the phase needs to add 3 dioptres on each pupil. Once the distance at which the refraction is going to be obtained is chosen, a scene (25) is displayed on screen (2).

This can be chosen from among a battery of images depending on the needs of the subject. The images can be the type of letters habitually employed during clinical practice for the measurement of visual sharpness. Landscapes, both natural and urban, may likewise be employed, especially for obtaining the refraction at long distances, Night time scenes may employed to the great benefit of those subjects who wish to obtain the refraction in low light conditions. For the refraction or the measurement of visual quality in general at mid and short distances, the scene can be adapted to real situations with which the subjects are faced in their daily lives.

The visual stimuli can also be presented in a monocular form by means of the occlusion of one of the eyes, in accordance with the methods disclosed above in relation to FIGS. 5 and 6 of the present document. The stimuli may likewise be shown with stereopsis or the sensation of volume, following the implementation described in reference to FIGS. 6 and 7. The possibility of refracting a subject by means of any scene that may be adapted to his needs and in a three dimensional manner represents a clinical advantage of the object phoropter of this invention. Once the scene and the manner of presenting it have been chosen (two or three dimensional) the process of seeking the refraction or most adequate visual correction begins. To do this the operator changes, in a controlled manner and following a previously established protocol, the blurring or astigmatism of each one of the pupils until obtaining the best vision under the initially selected conditions.

Figure 8:
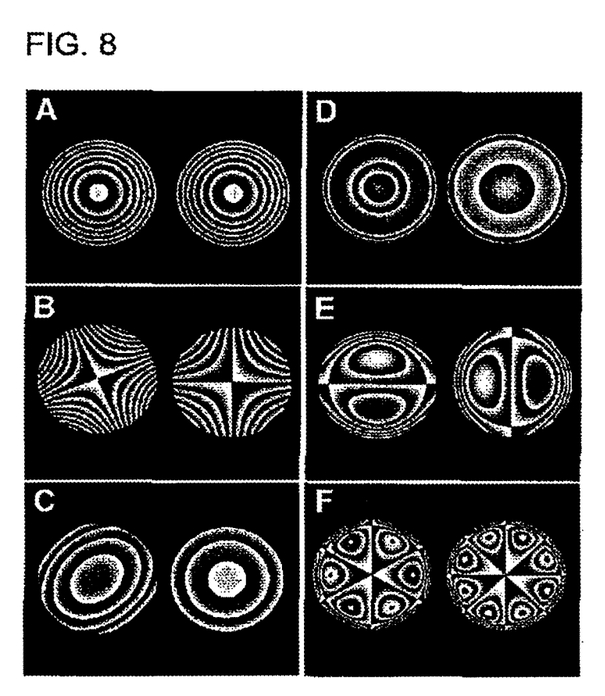
FIG. 8 shows, in the form of practical examples for illustrating the method disclosed in the present invention, different programmed phase profiles for the correction of the ametropias of the patient, the simulation of ophthalmic elements, and different visual conditions through the phoropter disclosed in the invention.

As a practical example, the left column FIG. 8 shows different situations corresponding to, from top to bottom, (A) pure myopic blurring of 1 dioptre, (B) regular astigmatism of 1 dioptre at 45 and 90 degrees, and (C) a combination of blurring and astigmatism of the right eye, and pure blurring of the left eye of 0.5 dioptres in each.

A singular feature of the instrument is the possibility of programming phase profiles corresponding to unusual visual corrections that differ from the standard ophthalmic lenses that are mounted in eyeglasses. A practical example are progressive eyeglasses, whose effect on the vision can be simulated as a step prior to acquiring them. In this way phase modulator (9) can also generate profiles corresponding to any type of intraocular lenses, such as progressive, diffractive, etc., before submitting the patient to surgical intervention. Personalized solutions can be tried in each case and the benefits they provide to each subject studied in a personalized manner.

An example of lenses that incorporate spherical aberration of opposite sign is shown in panel D in the right column of FIG. 8. The instrument can also be employed as a testing station for possible visual problems or the tolerance of the subject to off-centering of his optical corrections, including those that arise in the context of refractive surgery. An example of a coma aberration, vertical in one eye and horizontal in the other, is shown in pane E in the right column of FIG. 8. As a final example, panel F in the right column of FIG. 8 is displayed showing the phase corresponding to Zernike polynomials 18 and 25, to demonstrate the potential of the phoropter for simulating conditions of vision through exotic optics or profiles.

Ophthalmic corrections of the highest order that are different from blurring and astigmatism can be obtained in a simple manner with the instrument, simulating their effect on the vision of the subject through the optical phase that they produce.

Thanks to electro-optic technology the phoropter enables the operator himself to be the subject who looks through it. To do this the instrument contains a specific software that enables searching for the best ophthalmic corrections in a simultaneous manner with the vision of the stimuli.

Although some embodiments of the invention have been described and depicted, it is obvious that modifications can be made to them within their scope, and that the invention should not be considered limited to said embodiments, but rather only to the content of the following claims.

The invention claimed is:

1. An ophthalmic instrument for measurement of ocular refraction and visual simulation of a subject, that enables binocular simultaneous presentation of visual stimuli and perception thereof through different phase profiles or aberrations, the ophthalmic instrument comprising:
    a system of presentation of binocular stimuli which includes two input pupils;
    a first output and a second output pupil; and
    only one phase modulator, which is optically conjugated with the two input pupils and the two output pupils,
    wherein the optical conjugation is accomplished through lenses or mirrors,
    wherein the one phase modulator independently and simultaneously manipulates a first phase of the first output pupil and a second phase of the second output pupil such that the first phase is the same or different from the second phase, and
    wherein operations of the measurement of refraction and simulation of ophthalmic elements or visual conditions done in binocular manner.

2. The ophthalmic instrument for measurement of ocular refraction and visual simulation in accordance with claim 1, wherein control of the phase modulator is done in a digital manner.

3. The ophthalmic instrument for measurement of ocular refraction and visual simulation in accordance with claim 1, wherein the presentation of binocular stimuli is done by a screen on which scenes are displayed.

4. The ophthalmic instrument for measurement of ocular refraction and visual simulation in accordance with claim 3, wherein the system of presentation of binocular stimuli further includes an objective that collimates light issuing from the screen.

5. The ophthalmic instrument for measurement of ocular refraction and visual simulation in accordance with claim 3, wherein the binocular stimuli coming from the screen are projected on retinas of the subject in a binocular manner, and are affected by the phase or aberrations introduced by the phase modulator.

6. The ophthalmic instrument for measurement of ocular refraction and visual simulation in accordance with claim 1, wherein the phase modulator is a device based on liquid crystal in reflection.

7. The ophthalmic instrument for measurement of ocular refraction and visual simulation in accordance with claim 1, wherein the phase modulator is a device based on liquid crystal in transmission.

8. An ophthalmic instrument for measurement of ocular refraction and visual simulation of a subject, that enables binocular simultaneous presentation of visual stimuli and perception thereof through different phase profiles or aberrations, the ophthalmic instrument comprising:
    a system of presentation of binocular stimuli which includes two input pupils;
    two output pupils; and
    only one phase modulator, which is optically conjugated with the two input pupils and the two output pupils,
    wherein the optical conjugation is accomplished through lenses or mirrors,
    wherein the phase modulator manipulates the phase over the two output pupils simultaneously,
    wherein operations of the measurement of refraction and simulation of ophthalmic elements or visual conditions done in binocular manner, and
    wherein the phase modulator is a deformable mirror.

9. The ophthalmic instrument for measurement of ocular refraction and visual simulation in accordance with claim 8, wherein the deformable mirror is of electrostatic type.

10. The ophthalmic instrument for measurement of ocular refraction and visual simulation in accordance with claim 8, wherein the deformable mirror is segmented and includes a matrix of independently controlled micro-mirrors.

11. The ophthalmic instrument for measurement of ocular refraction and visual simulation in accordance with claim 8, wherein the deformable mirror is magnetic.

12. The ophthalmic instrument for measurement of ocular refraction and visual simulation in accordance with claim 8, wherein the deformable mirror is bimorphic.

13. The ophthalmic instrument for measurement of ocular refraction and visual simulation in accordance with claim 1, wherein the perception of visual stimuli is stereoscopic or three dimensional.

14. The ophthalmic instrument for measurement of ocular refraction and visual simulation in accordance with claim 13, wherein the perception of visual stimuli is three dimensional, and
    wherein the three dimensional perception of visual stimuli is obtained by alternating occlusion of the eyes, synchronized with a presentation of stereoscopic images on a single screen for the presentation of visual stimuli.

15. The ophthalmic instrument for measurement of ocular refraction and visual simulation in accordance with claim 14, wherein occlusion is done by phase profiles programmed in the phase modulator.

16. An ophthalmic instrument for measurement of ocular refraction and visual simulation of a subject, that enables binocular simultaneous presentation of visual stimuli and perception thereof through different phase profiles or aberrations, the ophthalmic instrument comprising:
    a system of presentation of binocular stimuli which includes two input pupils;
    two output pupils; and
    only one phase modulator, which is optically conjugated with the two input pupils and the two output pupils,
    wherein the optical conjugation is accomplished through lenses or mirrors,
    wherein the phase modulator manipulates the phase over the two output pupils simultaneously,
    wherein operations of the measurement of refraction and simulation of ophthalmic elements or visual conditions done in binocular manner,
    wherein the perception of visual stimuli is three dimensional,
    wherein the three dimensional perception of visual stimuli is obtained by alternating occlusion of the eyes, synchronized with a presentation of stereoscopic images on a single screen for the presentation of visual stimuli, and
    wherein occlusion is done by controlled actuation of a matrix of micro-mirrors that actuate as the input pupils of the instrument.

17. The ophthalmic instrument for measurement of ocular refraction and visual simulation in accordance with claim 13, wherein the perception of visual stimuli is three dimensional, and wherein the three dimensional perception of visual stimuli is obtained by two objectives, each dedicated to one of two pupils of the subject, which receive light coming from two stereoscopic scenes displayed on a single screen.

18. An ophthalmic instrument for measurement of ocular refraction and visual simulation of a subject, that enables binocular simultaneous presentation of visual stimuli and perception thereof through different phase profiles or aberrations, the ophthalmic instrument comprising:

a system of presentation of binocular stimuli which includes two input pupils;
two output pupils; and
only one phase modulator, which is optically conjugated with the two input pupils and the two output pupils,
wherein the optical conjugation is accomplished through lenses or mirrors,
wherein the phase modulator manipulates the phase over the two output pupils simultaneously,
wherein operations of the measurement of refraction and simulation of ophthalmic elements or visual conditions done in binocular manner,
wherein the perception of visual stimuli is three dimensional, and
wherein the three dimensional perception of visual stimuli is obtained by two objectives, each dedicated to one of two pupils of the subject, which receive light coming from two stereoscopic scenes displayed on two different screens.

19. The ophthalmic instrument for measurement of ocular refraction and visual simulation in accordance with claim 1, wherein control of interpupillary distance is done by two prisms in reflection.

20. The ophthalmic instrument for measurement of ocular refraction and visual simulation in accordance with claim 1, wherein control of interpupillary distance is done by pairs of flat mirrors.

21. The ophthalmic instrument for measurement of ocular refraction and visual simulation in accordance with claim 1, wherein control of interpupillary distance is done by a combination of prisms and mirrors.

22. The ophthalmic instrument for measurement of ocular refraction and visual simulation in accordance with claim 1, wherein control of inclination of incident beams of light on pupils of the subject that make lines of vision coincide is done by the phase modulator.

23. The ophthalmic instrument for measurement of ocular refraction and visual simulation in accordance with claim 1, further comprising an auxiliary positioning subsystem to center pupils of the subject on the two output pupils of the instrument, the auxiliary positioning subsystem including a lens and an objective coupled to a camera, such that the camera is susceptible to simultaneously registering the two pupils of the eyes of the subject.

24. The ophthalmic instrument for measurement of ocular refraction and visual simulation in accordance with claim 1, further comprising a wavefront sensor for objective measurement of an optical quality of eyes of the subject in a binocular manner.

25. A method, comprising:
providing the ophthalmic instrument according to claim 1; and
measuring ocular refraction of eyes with the ophthalmic instrument of claim 1.

26. A method, comprising:
providing the ophthalmic instrument according to claim 1; and
simulating ophthalmic elements, or ophthalmic lens and interocular lenses with the ophthalmic instrument of claim 1.

27. A method, comprising:
providing the ophthalmic instrument according to claim 1; and
simulating vision through an optical element with the ophthalmic instrument of claim 1.

28. A method, comprising:
providing the ophthalmic instrument according to claim 1; and
obtaining adequate optical parameters for incorporating intraocular lenses based on personalized measurement of refraction, the obtaining being performed with the ophthalmic instrument of claim 1.

29. A method, comprising:
providing the ophthalmic instrument according to claim 1; and
obtaining adequate optical parameters for incorporating ophthalmic lenses based on personalized measurement of refraction, the obtaining being performed with the ophthalmic instrument of claim 1.

30. A method, comprising:
providing the ophthalmic instrument according to claim 1; and
obtaining adequate optical and geometric parameters for incorporating into refractive corrections done by surgery of a cornea based on personalized measurement of refraction, the obtaining being performed with the ophthalmic instrument of claim 1.

31. A method, comprising:
providing the ophthalmic instrument according to claim 1; and
simulating vision following a surgical intervention in an eye with the ophthalmic instrument of claim 1.

32. A method, comprising:
providing the ophthalmic instrument according to claim 1; and
simulating vision following a refractive surgical operation with the ophthalmic instrument of claim 1.

* * * * *